US00PP13573P2

(12) United States Plant Patent
Brown

(10) Patent No.: US PP13,573 P2
(45) Date of Patent: Feb. 18, 2003

(54) AGLAONEMA PLANT NAMED 'CAMOUFLAGE'

(75) Inventor: B. Frank Brown, Malabar, FL (US)

(73) Assignee: Sunshine Foliage World, Zolfo Springs, FL (US)

( * ) Notice: Subject to any disclaimer, the term of this patent is extended or adjusted under 35 U.S.C. 154(b) by 0 days.

(21) Appl. No.: 10/094,282

(22) Filed: Mar. 8, 2002

(51) Int. Cl.[7] ..... A01H 5/00
(52) U.S. Cl. ..... Plt./376

(58) Field of Search ..... Plt./376

*Primary Examiner*—Kent L. Bell
(74) *Attorney, Agent, or Firm*—C. A. Whealy

(57) ABSTRACT

A distinct cultivar of Aglaonema plant named 'Camouflage', characterized by its upright and outwardly arching growth habit; freely clumping habit; broad oblong leaves with acuminate apices; tri-colored leaves with contrasting dark and mid-green chevrons on a light green background with random dark and mid-green spots and flecks, surrounded by a dark green margin; whitish green leaf petioles with random green spots and flecks; and tolerance to low temperatures.

1 Drawing Sheet

BOTANICAL CLASSIFICATION/CULTIVAR DENOMINATION

*Aglaonema crispum*×*Aglaonema treubii* cultivar 'Camouflage'.

BACKGROUND OF THE INVENTION

The present Invention relates to a new and distinct cultivar of Aglaonema plant, botanically known as *Aglaonema crispum*×*Aglaonema treubii* and hereinafter referred to by the name 'Camouflage'.

The new Aglaonema is the result of a planned breeding program conducted by the Inventor in Malabar, Fla. The objective of the breeding program is to create new freely clumping Aglaonema cultivars with broad leaves and low temperature tolerance.

The new Aglaonema originated from a cross-pollination made by the Inventor on Aug. 10, 1996 of an unnamed selection of *Aglaonema crispum*, not patented, as the female, or seed, parent with an unnamed selection of *Aglaonema treubii*, not patented, as the male, or pollen, parent. The new Aglaonema was discovered and selected by the Inventor in 1997 as a single plant within the progeny of the stated cross in a controlled environment in Malabar, Fla. The new Aglaonema was selected on the basis of its freely clumping habit, broad leaves and low temperature tolerance.

Asexual propagation of the new cultivar by cuttings since Jul. 11, 1998 in a controlled environment in Malabar, Fla., has shown that the unique features of this new Aglaonema are stable and reproduced true to type in successive generations.

SUMMARY OF THE INVENTION

The following traits have been repeatedly observed and are determined to be the unique characteristics of 'Camouflage'. These characteristics in combination distinguish 'Camouflage' as a new and distinct cultivar:

1. Upright and outwardly arching growth habit.
2. Freely clumping habit, full and dense plants.
3. Broad oblong leaves with acuminate apices.

4. Tri-colored leaves with contrasting dark and mid-green chevrons on a light green background with random dark and mid-green spots and flecks, surrounded by a dark green margin.
5. Whitish green leaf petioles with random green spots and flecks.
6. Tolerant to low temperatures.

In side-by-side comparisons conducted by the Inventor in Malabar, Fla., plants of the new Aglaonema differed from plants of the female parent, the unnamed selection of *Aglaonema crispum*, in the following characteristics:

1. Plants of the new Aglaonema were more freely clumping than plants of the female parent.
2. Plants of the new Aglaonema had more closely spaced leaves and appeared to be fuller and denser in appearance than plants of the female parent.
3. Leaves of plants of the new Aglaonema were more broad than leaves of plants of the female parent.
4. Leaves of plants of the new Aglaonema had more distinct chevrons than leaves of plants of the female parent.

In side-by-side comparisons conducted by the Inventor in Malabar, Fla., plants of the new Aglaonema differed from plants of the male parent, the unnamed selection of *Aglaonema treubii*, in the following characteristics:

1. Plants of the new Aglaonema were more freely clumping than plants of the male parent.
2. Plants of the new Aglaonema were larger and faster growing than plants of the male parent.
3. Leaves of plants of the new Aglaonema were more broad than leaves of plants of the male parent.

Plants of the new Aglaonema can be compared to plants of the Aglaonema cultivar 'B.J. Freeman', disclosed in U.S. Plant Pat. No. 6,857. In side-by-side comparisons conducted by the Inventor in Malabar, Fla., plants of the new Aglaonema differed from plants of the Aglaonema cultivar 'B.J. Freeman' in the following characteristics:

1. Plants of the new Aglaonema were more outwardly arching than plants of the 'B.J. Freeman'.
2. Leaves of plants of the new Aglaonema were more broad and shorter than leaves of plants of the 'B.J. Freeman'.

3. Leaves of plants of the new Aglaonema had a more distinct variegation pattern and chevrons than leaves of plants of the 'B.J. Freeman'.

4. Plants of the new Aglaonema were more tolerant to low temperatures than plants of the cultivar 'B.J. Freeman'.

BRIEF DESCRIPTION OF THE PHOTOGRAPHS

The accompanying colored photographs illustrate the overall appearance of the new Aglaonema, showing the colors as true as it is reasonably possible to obtain in colored reproductions of this type. Colors in the photographs may differ slightly from the color values cited in the detailed botanical description which accurately describe the colors of the new Aglaonema.

The photograph at the top of the sheet comprises a side perspective view of a typical plant of 'Camouflage'.

The photograph at the bottom of the sheet comprises a close-up view of the upper surfaces of a typical young leaf (top) and a typical fully expanded leaf (bottom) of the new Aglaonema.

DETAILED BOTANICAL DESCRIPTION

The cultivar 'Camouflage' has not been observed under all possible environmental conditions. The phenotype may vary somewhat with variations in environment such as temperature and light intensity without, however, any variance in genotype.

The aforementioned photographs and following observations and measurements were taken in October, 2001, and describe plants of the new Aglaonema that were grown in 25-cm containers, in Zolfo Springs, Fla. in a polyethylene-covered shadehouse with 86 percent shading. During the production of the plants, day temperatures averaged 80° F. and night temperatures averaged 65° F. Plants used for the photographs and description were about 11 months from planting. Color references are made to The Royal Horticultural Society Colour Chart, 1995 Edition, except where general terms of ordinary dictionary significance are used.

Botanical classification: *Aglaonema crispum*×*Aglaonema treubii* cultivar 'Camouflage'.

Parentage:

*Female, or seed, parent.*—Unnamed selection of *Aglaonema crispum*, not patented.

*Male, or pollen, parent.*—Unnamed selection of *Aglaonema treubii*, not patented.

Propagation:

*Type.*—By cuttings.

*Time to initiate roots.*—Summer: About 39 days at 85° F. Winter: About 62 days at 59° F.

*Time to produce a rooted plant.*—Summer: About 44 days at 85° F. Winter: About 73 days at 59° F.

*Root description.*—Thick, fleshy, and freely-branching; white in color.

Plant description:

*Appearance.*—Erect when young, becoming upright and outwardly arching as leaves develop; inverted triangle, symmetrical. Freely clumping habit and closely-spaced leaves give plants a very fully and dense appearance. Appropriate for 25-cm containers.

*Plant height.*—About 57 cm.

*Plant width.*—About 76 cm.

*Growth rate/vigor.*—Vigorous, rapid growth rate.

*Stem color.*—143A to 144A.

*Branching habit.*—Freely clumping habit; plants typically produce about six offshoots per plant; full and dense plants.

*Foliage description.*—Length: About 28.25 cm. Width: About 14.5 cm. Shape: Broadly oblong. Apex: Acuminate. Base: Obtuse. Margin: Entire, slightly undulating. Orientation: Initially upright to outwardly arching. Aspect: Undulating. Texture, upper and lower surfaces: Mostly smooth, slightly rugose; glabrous; thick and leathery. Luster: Young leaves, upper and lower surfaces: Glossy. Fully expanded leaves, upper surface: Glossy. Fully expanded leaves, lower surface: Slightly glossy. Veins: Slightly recessed on upper surface and prominent on lower surface. Color: Young leaves, upper surface: Tri-colored with contrasting dark green and mid-green chevrons on a light green background with random dark and mid-green spots and flecks, surrounded by a dark green margin. Dark green coloration: between darker than 144A to more green than 146A; mid-green coloration: more green than 147B; and light green coloration: closest to 148C. Young leaves, lower surface: Closest to 146B. Fully expanded leaves, upper surface: Tri-colored with contrasting dark green and mid-green chevrons on a light green background with random dark and mid-green spots and flecks, surrounded by a dark green margin. Dark green coloration: more green than 147A; mid-green coloration: closest to 191A; and light green coloration: between 191C and 148C. Fully expanded leaves, lower surface: Between 146A and 146B. Venation, upper surface: Midvein, 145C with random speckles of 143A; lateral veins, same as ground color. Venation, lower surface: Closest to 145D. Petiole: Length: About 15 cm. Diameter, at leaf base: About 6 mm. Diameter, at stem attachment: About 1.6 cm. Wing length: About 13 cm. Wing width, at base: About 8 mm. Color: Towards the leaf, close to 145D; towards the stem, 158B to 158C; random green, 143A to 144A, spots and flecks mostly along the wings.

Inflorescence description: Inflorescence development has not been observed on plants of the new Aglaonema grown under shadehouse production conditions.

Disease resistance: Plants of the new Aglaonema have not been observed to be resistant to pathogens common to Aglaonema.

Pest resistance: Plants of the new Aglaonema have been observed to be resistant to mealy bugs, red spider mites and scale.

Temperature tolerance: Plants of the new Aglaonema have been observed to be tolerant to temperatures from 40 to 100° F.

It is claimed:

1. A new and distinct cultivar of Aglaonema plant named 'Camouflage', as illustrated and described.

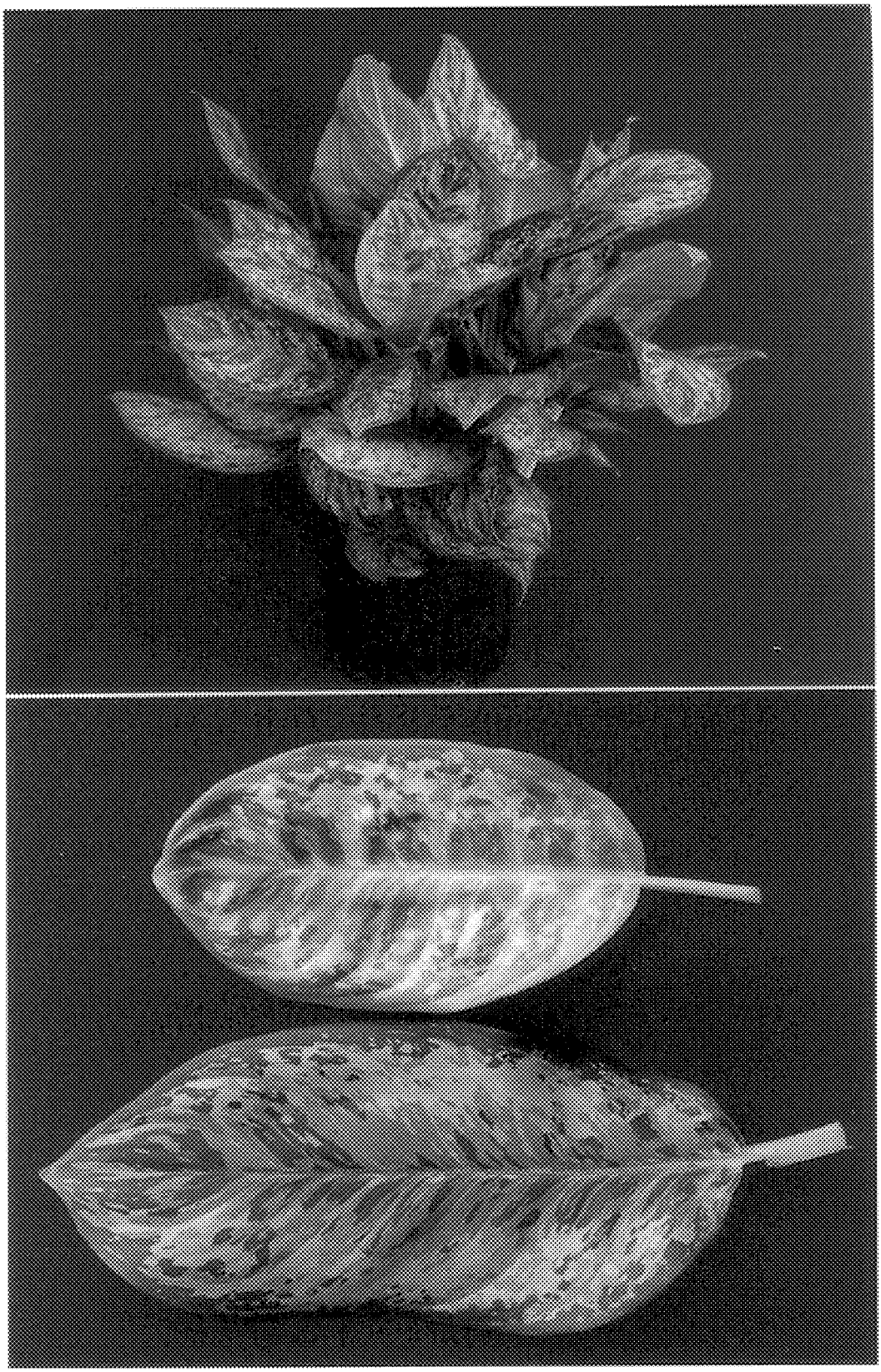

* * * * *